United States Patent [19]

Shimizu et al.

[11] Patent Number: 4,620,056
[45] Date of Patent: Oct. 28, 1986

[54] METHOD FOR PRODUCING AROMATIC HYDROCARBONS

[75] Inventors: Isoo Shimizu; Hideki Nomura; Kazumichi Uchida, all of Yokohama; Hitoshi Mitsuyuki, Kawasaki, all of Japan

[73] Assignee: Nippon Petrochemicals Co., Ltd., Tokyo, Japan

[21] Appl. No.: 770,506

[22] Filed: Aug. 28, 1985

[30] Foreign Application Priority Data

Aug. 29, 1984 [JP] Japan ................. 59-179977

[51] Int. Cl.$^4$ .............................. C07C 2/64
[52] U.S. Cl. ..................... 585/452; 585/453
[58] Field of Search .................. 585/452, 453

[56] References Cited

U.S. PATENT DOCUMENTS 2,849,508 8/1958 Pines ........................ 585/453
3,651,161 3/1972 Waragai et al. ............ 585/452
4,179,472 12/1979 Cobb .......................... 585/452

FOREIGN PATENT DOCUMENTS 1269280 4/1972 United Kingdom ........... 585/452

Primary Examiner—Curtis R. Davis
Attorney, Agent, or Firm—Scully, Scott, Murphy & Presser

[57] ABSTRACT

A method for producing an aromatic hydrocarbon easily and safely without the use of carrier-supported catalyst and is characterized in that an unsaturated compound having a double bond or bonds that are conjugated with the benzene ring is allowed to coexist in the process to alkylate a substituted aromatic hydrocarbon with olefins in the presence of 5 mM or more of metallic sodium and potassium compound to provide 3 mM or more of potassium ions relative to 1 mole of the substituted aromatic hydrocarbon, said substituted aromatic hydrocarbon having at least one alkyl group or alkylene group which has at least one hydrogen atom in the α-position relative to the aromatic ring of said substituted aromatic hydrocarbon.

5 Claims, 1 Drawing Figure

METHOD FOR PRODUCING AROMATIC HYDROCARBONS

BACKGROUND OF THE INVENTION (1) Field of the Invention

This invention relates to a method for producing aromatic hydrocarbons by introducing alkyl groups into alkyl or alkylene side chains of substituted aromatic hydrocarbons. More particularly, the invention relates to a novel method for alkylating side chains of substituted aromatic hydrocarbons with ethylene and/or propylene in the presence of metallic sodium catalyst.

(2) Description of the Prior Art

As the methods for producing new aromatic compounds by alkylating side chains of aromatic compounds with alkali metal catalysts, there are disclosed several examples of reactions in Herman Pines, "Base Catalyzed Reactions of Hydrocarbons and Related Compounds", Academic Press, New York.

Furthermore, there are prior art disclosures on the alkylation reaction of side chains using alkali metal catalysts: British Pat. No. 857,894 in which alkali metals and iron compounds are used; J. Amer. Chem. Soc., 82, 4912 (1960) and J. Org. Chem., 22, 48 (1957) in which polycyclic aromatic compounds are used as promoters; and British Pat. No. 1,269,280 in which alkali metals carried on potassium compounds are used.

When the above carrier-supported catalysts are used for chemical reaction, it is necessary to put catalysts on carriers beforehand.

In the field to deal with metallic sodium, the danger of metallic sodium is well known. From this fact, it is not too much to say that to accomplish the method of handling the metallic sodium safely is inevitable for carrying out the reaction using the metallic sodium in the chemical industry in which large quantities of inflammable substances are employed. From the viewpoint of the possible industrial practice to put the dangerous metallic sodium on fine carrier particles, it is necessary to pay close attention to the handling of metallic sodium as well as to several apparatus in order to avoid the inflammation when not only a trace quantity of water but also a very small quantity of oxygen exist.

That is, all of the above processes to put the metallic sodium on carriers, are done without the presence of any solvent, the so-called dry process. The dry process, however, involves the danger of spontaneous combustion of metallic sodium. Meanwhile, a method to use liquid ammonia as a solvent has been proposed, however, it also involves much difficulty in the pretreatment and the handling of liquid ammonia.

BRIEF SUMMARY OF THE INVENTION

In view of the above-described state of the conventional art, it is the primary object of the present invention to provide a safe method for producing aromatic hydrocarbons, in which the activity of carrier-supported catalyst is higher than the conventional ones and the danger of combustion of metallic sodium is smaller.

Another object of the present invention is to provide a simple and easy method which substantially requires neither pretreatment nor catalyst-loading treatment.

According to the present invention, the method for producing an aromatic hydrocarbon is characterized in that an unsaturated compound having a double bond or bonds that are conjugated with the benzene ring of said unsaturated compound is allowed to coexist in the process to alkylate a substituted aromatic hydrocarbon with ethylene and/or propylene in the presence of 5 mM (millimoles) or more of metallic sodium relative to 1 mole of said substituted aromatic hydrocarbons and at least one member selected from the group consisting of potassium carbonate, potassium hydrogen carbonate and potassium hydroxide which is sufficient to provide 3 mM or more of potassium ions also relative to 1 mole of said substituted aromatic hydrocarbon, said substituted aromatic hydrocarbon having at least one alkyl group or alkylene group which has at least one hydrogen atom in $\alpha$-position relative to the aromatic ring of said substituted aromatic hydrocarbon.

DETAILED DESCRIPTION OF THE INVENTION

Figure 1:
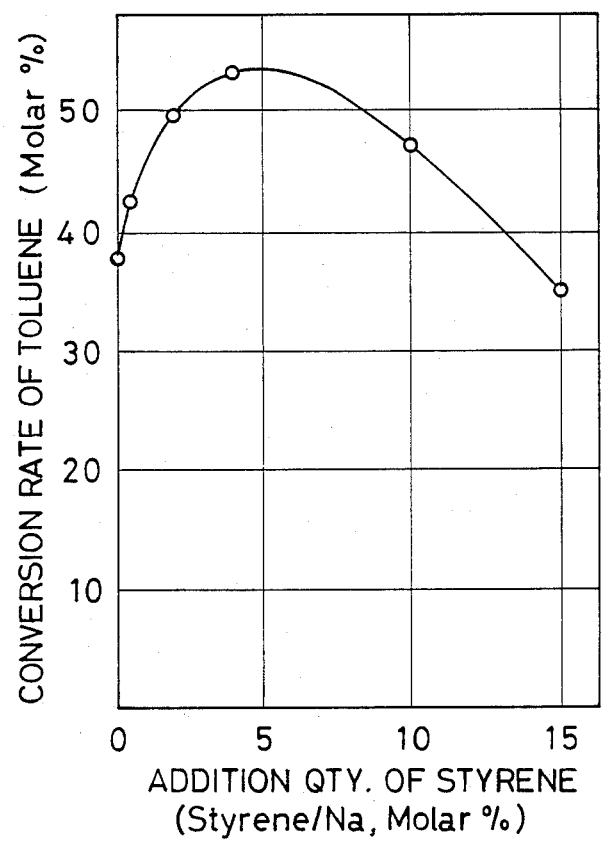
FIG. 1 is a graphic chart showing the relation between conversion rates of toluene and addition quantities of styrene in the test results of Example 2.

The foregoing substituted aromatic hydrocarbons to be alkylated by ethylene and/or propylene have at least one alkyl group or alkylene group which has at least one hydrogen atom in $\alpha$-position relative to the aromatic ring. The alkylation is done by joining the ethylene or propylene to the above alkyl group or alkylene group in the $\alpha$-position.

The substituted aromatic hydrocarbons include monocyclic aromatic hydrocarbons and condensed polycyclic aromatic hydrocarbons. Exemplified as the groups that are joined to the aromatic hydrocarbons are $C_1$ to $C_8$ alkyl groups such as methyl, ethyl, n-propyl, isopropyl, n-butyl, isobutyl, sec-butyl, n-amyl, isoamyl and sec-amyl groups. These substituent groups have a hydrogen atom in the $\alpha$-position relative to the aromatic hydrocarbon. While, a plurality of these alkyl groups can be joined to the substituted aromatic hydrocarbon. The alkylene groups are divalent groups in which two hydrogen atoms are removed from $C_2$ to $C_8$ saturated hydrocarbons and these also should have a hydrogen atom in the $\alpha$-position relative to the aromatic ring. These alkylene groups may constitute cyclic polymethylene side chains such as those in tetralin and indane.

The substituted aromatic hydrocarbons are exemplified by monocyclic aromatic hydrocarbons having alkyl groups such as toluene, ethylbenzene, n-propylbenzene, isopropylbenzene, n-butylbenzene, isobutylbenzene, sec-butylbenzene, n-amylbenzene, isoamylbenzene, sec-amylbenzene, $\alpha,\alpha'$-diethyltoluene, o-, m- and p-xylene, o-, m- and p-diethylbenzene, o-, m- and p-isopropyltoluene, and cymene.

Exemplified as the substituted aromatic hydrocarbons having a cyclic polymethylene side chain as an alkylene group are indane, alkylindanes such as 1-methylindane, 1,1-dimethylindane, 1,1,3-trimethylindane, 1-ethylindane, 1,1-diethylindane and 1,1,3-triethylindane, tetralin and alkyltetralins such as 1-methyltetralin, 1,1-dimethyltetralin and 1,1,4-trimethyltetralin.

The olefins used for the alkylation of side chains are ethylene, propylene or their mixture. When $C_4$ or higher olefins are used in the method of the present invention, the reaction is very slow even when reaction conditions are made so severe that the aromatic starting materials are decomposed, and the polymerization of olefins is markedly caused to occur. Accordingly, it is substantially impossible to carry out the method industrially using the C₄ or higher olefins.

The metallic sodium as one catalytic material in the method of the present invention can be fed onto a reaction system in any physical state before use. That is, it may be any of solid state and fused state. Furthermore, the metallic sodium in the state of fine particles which are dispersed in a solvent, the so-called sodium dispersion, can also be used. It is desirable, however, to use the metallic sodium in a solid state in view of the easiness and safety in handling.

The use quantity of the metallic sodium is 5 mM or more relative to 1 mole of substituted aromatic hydrocarbon. If the quantity of metallic sodium is less than 5 mM, reactivity is undesirably impaired. There is no upper limit with regard to the use quantity, however, the excessive use of catalyst is undesirable because of the problems in the heat generation in the deactivation of catalyst and accompanying increase in the cooling of reaction system and the treatment of strong alkaline waste. Furthermore, even when a catalyst is used in excess, the whole catalyst does not work only with the lowering of overall catalytic efficiency. Accordingly, it is not necessary to use more than 200 mM of the catalyst relative to 1 mole of the substituted aromatic hydrocarbon.

The other catalyst is a potassium compound selected from the group consisting of potassium carbonate, potassium hydrogen carbonate and potassium hydroxide. These compounds can be used also in a mixture. It is desirable that they are used by being dried to anhydrous state. The potassium compounds can be employed singly or in a state carried on other inert carriers by impregnation or by mixing. The carriers are substances that are inert to the alkylation reaction and the sodium such as diatomaceous earth, pumice, activated carbon and graphite.

The use quantity of potassium compound is 3 mM or more as potassium ions relative to 1 mole of the substituted aromatic hydrocarbon. If the quantity of potassium ions is less than 3 mM, sufficient alkylation activity cannot be expected.

There is no upper limit with regard to the use quantity of potassium compounds, however, it is to be determined according to the cost necessary for the treatment of alkaline waste which is produced by the deactivation of the catalyst. In practice, it is not necessary to use more than about 300 mM of potassium compound relative to 1 mole of the substituted aromatic hydrocarbon.

The unsaturated compounds to coexist are unsaturated aromatic hydrocarbons having olefinic carbon-carbon double bonds which are conjugated with benzene rings. The number of double bonds joined to a benzene ring in an unsaturated compound can be plural, that is, the number of double bonds can be selected arbitrary. The compounds having one double bond that is conjugated to benzene ring, are exemplified by styrene and alkyl-substituted styrenes such as α-methylstyrene, β-methylstyrene and vinyltoluene. Besides them, there are indene and alkylindenes that have cyclic double bonds. The unsaturated compound having two double bonds is exemplified by divinylbenzene which is desirable because it is easily available.

The unsaturated compound to coexist can be added to the reaction system at any time before the introduction of the olefin for alkylation. In practice, it is preferable in view of safety that the unsaturated compound is added simultaneously with the addition of the metallic sodium and the potassium compound because the temperature of reaction system is low. The addition quantity of the unsaturated compound is from 0.5% to 15% by mole relative to the metallic sodium. When the quantity of unsaturated compound is less than 0.5% by mole, the effect of addition cannot be expected to occur, meanwhile, if the quantity of unsaturated compound is more than 15% by mole, the catalytic activity becomes all the lower than the case in which the unsaturated compound is not used. Accordingly, neither of them is desirable. Even though the reason for the effect brought about is not clear, it is certain that the efficiency of alkylation can be much improved by adding a proper quantity of the unsaturated compound.

In the method of the present invention, the metallic sodium, the potassium compound and the unsaturated compound added to a reaction system must be stirred together in an aromatic hydrocarbon at 120° C. or above, before the alkylation or during the alkylation. When this stirring is carried out in other solvents, for example, an aliphatic hydrocarbon such as octane or polar solvents such as ether that is inert to metallic sodium, it is not desirable because the metallic sodium and the potassium compound remain separated from each other. The aromatic hydrocarbons may be any of the foregoing substituted aromatic hydrocarbons and other aromatic hydrocarbons such as benzene and alkylbenzenes such as tert-butylbenzene and tert-amylbenzene having no hydrogen atom in the α-position of a side chain.

The temperature of stirring treatment is 120° C. or above in order to fuse and fluidize the metallic sodium. There is no upper limit of this temperature, however, the stirring is carried out, in practice, below 260° C.

The stirring treatment can be carried out by a stirrer or agitator, preferably at a stirring velocity of 0.5 m/sec or higher. If the stirring velocity is too low, the fused metal particles easily aggregate which invites the lowering of catalytic efficiency. When the stirring is done with stirring blades, the velocity of stirring is represented by the linear velocity of the free end of a stirring blade. The time of stirring treatment is not limited here.

After the stirring treatment, it is preferable that the mixture of the metallic sodium, potassium compound and unsaturated compound obtained by the stirring treatment is used as it stands together with the aromatic hydrocarbon for the next alkylation.

As described in the foregoing passage, the substituted aromatic hydrocarbons to be alkylated can also be used as the aromatic hydrocarbons for the stirring treatment. Accordingly, it is the most preferable mode of the present invention that the above stirring treatment is done using a substituted aromatic hydrocarbon to be alkylated. More particularly, predetermined quantities of metallic sodium, potassium compound, unsaturated compound and substituted aromatic hydrocarbon are fed into a reaction vessel and subjected to stirring. During the stirring or after the stirring, an olefin for alkylation is introduced into the reaction vessel and the alkylation is carried out by raising the pressure and the temperature, if needed, to predetermined levels.

The temperature of alkylation is 120° C. or above. The reaction does not proceed at temperatures below 120° C. A higher reaction temperature reduces the reaction time, however, if the reaction temperature is too high, for example higher than 260° C., the starting aromatic hydrocarbon and the olefin are carbonized and the carbonized products deposit on the surfaces of catalyst to inhibit the reaction. Furthermore, the complete deactivation of the carbon deposited catalyst sodium becomes difficult in the deactivation step after the reaction. Accordingly, it is desirable that the reaction is carried out at temperatures in the range of 120° C. to 260° C.

The reaction proceeds under pressures of 5 kg/cm$^2$ or above. Pressures below 5 kg/cm$^2$ are not desirable because the rate of reaction is markedly lowered. Higher pressures can accelerate the reaction, however, a higher pressure-withstanding level is required of a reaction vessel. In practice, pressures below 70 kg/cm$^2$ are preferably employed. For pressurization, an olefin such as ethylene or propylene is previously fed into a reaction vessel and the pressure is raised by heating, or the pressure is elevated and maintained by continuously feeding the olefin using a high-pressure pump. The olefin can be fed in a state of gas or liquid in the method of the present invention.

In the alkylation, the foregoing aromatic hydrocarbons and the starting substituted aromatic hydrocarbons can be used as reaction solvents. Besides them, other solvents that are inert to the alkylation and the metallic sodium, for instance, paraffins such as hexane and octane and cycloparaffins such as decalin can also be used as solvents.

The reaction time of the alkylation is not especially limited, however, it is generally in the range of 1 to 50 hours.

After the reaction, if necessary, the catalyst is deactivated with an alcohol such as methanol and ethanol or water, and the reaction mixture is rinsed with water, which is followed by distillation to obtain an aimed alkylated product.

In the method of the present invention, even though neither the pretreatment of catalyst nor the catalyst-loading on a carrier is required at least in a preferable mode, the catalytic efficiency is higher as compared with known carrier-supported catalysts.

In addition, the method is quite safe because it is not necessary at all to handle the dangerous metallic sodium outside the reaction system.

The present invention will be described in more detail with reference to several examples.

EXAMPLE 1

To a 0.5 liter autoclave with a stirrer are added 138 g (1.5 mole) of toluene, 0.6 g (26 mM) of solid metallic sodium, 6 g (40 mM) of potassium carbonate, and 0.054 g (0.52 mM) of styrene. They were heated to 180° C. with stirring. After the heating, the contents were pressurized to 35 kg/cm$^2$ with propylene and reaction was carried out for 24 hours. After the reaction, the reaction mixture was cooled to room temperature, unreacted propylene was then discharged, and the catalysts were deactivated by adding 10 ml of methyl alcohol with stirring for 30 minutes. The reaction mixture was then rinsed with water until it was neutralized to obtain 206 g of an oily mixture. The results of this experiment are shown in the following Table 1.

COMPARATIVE EXAMPLE 1

A carrier-supported catalyst (metallic sodium was carried on potassium carbonate) was prepared by mixing powder of anhydrous potassium carbonate with fused metallic sodium in an atmosphere of dry nitrogen at 300° C. and the mixing was continued for 2 hours at the same temperature. The quantity of the metallic sodium was Na/K$_2$CO$_3$=1/10 by weight.

This carrier-supported catalyst (6.6 g) and 138 g of toluene were fed into the same autoclave as that in Example 1 and reaction was carried out likewise to obtain 173 g of an oily mixture. The results are also shown in the following Table 1.

COMPARATIVE EXAMPLE 2

Reaction was carried out in the like manner as Example 1 except that styrene was not used to obtain 181 g of an oily mixture. The results are also shown in the following Table 1.

TABLE 1

| Item | Example 1 | Comp. Example 1 | Comp. Example 2 |
|---|---|---|---|
| Composition (wt. %) | | | |
| Hexene | 10.4 | 5.6 | 7.1 |
| Toluene | 20.9 | 46.8 | 42.1 |
| Isobutylbenzene | 60.9 | 43.3 | 46.0 |
| n-Butylbenzene | 3.9 | 2.1 | 2.2 |
| Heavier Products | 3.8 | 2.2 | 2.7 |
| Catalytic Efficiency(*) | 19.0 | 11.3 | 12.6 |
| Conversion Rate of Toluene (Molar %) | 69 | 41 | 45 |

Note(*): Isobutylbenzene (g)/Catalyst (g)

EXAMPLE 2

Toluene and propylene were reacted in the like manner as Example 1 where the addition quantity of styrene was varied in 16 hours' reaction time after the pressurizing with propylene. The main reaction product was isobutylbenzene in the whole procedure.

The relation between the conversion rates of toluene and addition quantities of styrene is shown in the attached FIG. 1.

EXAMPLE 3

Alkylation with ethylene was carried out using 1.5 mole of substituted aromatic hydrocarbons, 0.5 mM of unsaturated compounds, 6 g (40 mM) of potassium carbonate, and 0.6 g (26 mM) of solid metallic sodium. The reaction conditions were temperature: 180° C., pressure' 30 kg/cm$^2$ and time: 16 hours. The results thereof are shown in the following Table 2.

Beside the above experiments, similar tests were carried out without using the unsaturated compound. As a result, it was understood that the conversion rates of substituted aromatic hydrocarbons were lower by 20 to 40% of those values in the above experiments. In addition, the lowering in the yields of main products was more serious.

TABLE 2

| Number | Substituted Aromatic Hydrocarbon | Unsaturated Compound | Main Products | Conversion Rate(*) |
|---|---|---|---|---|
| 3-1 | Ethylbenzene | α-Methylstyrene | Isobutylbenzene, tert-Hexylbenzene | 60 |
| 3-2 | Isopropylbenzene | β-Methylstyrene | tert-Amylbenzene | 85 |
| 3-3 | Isopropylbenzene | Vinyltoluene | tert-Amylbenzene | 83 |
| 3-4 | Isopropylbenzene | Indene | tert-Amylbenzene | 77 |
| 3-5 | Isopropylbenzene | Divinylbenzene | tert-Amylbenzene | 69 |

TABLE 2-continued

| Number | Substituted Aromatic Hydrocarbon | Unsaturated Compound | Main Products | Conversion Rate(*) |
|---|---|---|---|---|
| 3-6 | sec-Butylbenzene | Styrene | tert-Hexylbenzene | 49 |
| 3-7 | p-Xylene | Styrene | 4-n-Propyltoluene p-di-n-Propylbenzene | 53 |
| 3-8 | p-Cymene | Styrene | 4-t-Amyltoluene | 75 |
| 3-9 | 1,1-Dimethylindane | Styrene | 1,1-Dimethyl-3-ethylindane 1,1-Dimethyl-3,3-diethylindane | 60 |
| 3-10 | α-Methylnaphthalene | Styrene | α-Propylnaphthalene | 28 |

Note(*): Conversion rate of substituted aromatic hydrocarbon (molar %).

EXAMPLE 4

Reaction was carried out in the like manner as Example 1 with using each potassium compound shown in the following Table 3 as one component of the catalysts. The use quantity of the potassium compound was 0.08 mole as potassium ions.

The reaction conditions were temperature: 180° C., pressure: 40 kg/cm² and time: 16 hours. The results are also shown in Table 3.

From the results in the foregoing examples, it is understood that the conversion rate is extremely lowered when potassium compound is not added (No. 4-3). Furthermore, the effect of addition of potassium compound can be hardly observed in the potassium compounds other than potassium carbonate, potassium hydrogen carbonate and potassium hydroxide.

TABLE 3

| Number | Potassium Compound | Main Product | Conversion Rate(*) |
|---|---|---|---|
| 4-1 | KHCO$_3$ | Isobutylbenzene | 53 |
| 4-2 | KOH | Isobutylbenzene | 49 |
| 4-3 | (None) | Isobutylbenzene | 3.4 |
| 4-4 | K$_2$SO$_4$ | Isobutylbenzene | 9.1 |
| 4-5 | KNO$_3$ | Isobutylbenzene | 0.4 |
| 4-6 | KCl | Isobutylbenzene | 2.4 |
| 4-7 | KI | Isobutylbenzene | 3.3 |
| 4-8 | KSCN | Isobutylbenzene | 0.2 |
| 4-9 | CH$_3$COOK | Isobutylbenzene | 1.1 |

Note(*): Conversion rate of toluene (molar %)

What is claimed is:

1. A method for producing an aromatic hydrocarbon which is characterized in that an unsaturated compound having a double bond or bonds that are conjugated with the benzene ring of said unsaturated compound is allowed to coexist in the process to alkylate a substituted aromatic hydrocarbon with ethylene and/or propylene in the presence of 5 mM (millimoles) or more of metallic sodium relative to 1 mole of said substituted aromatic hydrocarbons and at least one member selected from the group consisting of potassium carbonate, potassium hydrogen carbonate and potassium hydroxide which is sufficient to provide 3 mM or more of potassium ions also relative to 1 mole of said substituted aromatic hydrocarbon, said substituted aromatic hydrocarbon having at least one alkyl group or alkylene group which has at least one hydrogen atom in the α-position relative to the aromatic ring of said substituted aromatic hydrocarbon.

2. The method in claim 1, wherein said unsaturated compound is at least one member selected from the group consisting of styrene, α-methylstyrene, β-methylstyrene, vinyltoluene, indene, alkylindene and divinylbenzene.

3. The method in claim 1 or 2, wherein the quantity of said unsaturated compound is in the range of 0.5 to 15% by mole relative to said metallic sodium.

4. The method in claim 1, wherein the substituted aromatic hydrocarbon is at least one member selected from the group consisting of toluene, ethylbenzene, isopropylbenzene, sec-butylbenzene, xylene, cymene, 1,1-dimethylindane and α-methylnaphthalene.

5. The method of claim 1, wherein said metallic sodium is not carried on the potassium carbonate, potassium hydrogen carbonate or potassium hydroxide when being fed into the reaction system.

* * * * *